United States Patent
Peddle

(10) Patent No.: US 10,527,531 B2
(45) Date of Patent: Jan. 7, 2020

(54) BALL DROP IRIS FOR VERTICAL IMPACT TESTING

(71) Applicant: UNITED STATES GYPSUM COMPANY, Chicago, IL (US)

(72) Inventor: Robert T. Peddle, Lake Villa, IL (US)

(73) Assignee: UNITED STATES GYPSUM COMPANY, Chicago, IL (US)

(*) Notice: Subject to any disclaimer, the term of this patent is extended or adjusted under 35 U.S.C. 154(b) by 269 days.

(21) Appl. No.: 15/414,424

(22) Filed: Jan. 24, 2017

(65) Prior Publication Data

US 2018/0209884 A1 Jul. 26, 2018

(51) Int. Cl.
*G01N 3/303* (2006.01)

(52) U.S. Cl.
CPC .................. *G01N 3/303* (2013.01)

(58) Field of Classification Search
CPC ............ G01N 3/303; G01N 3/52; G01M 7/08
USPC ........................................ 73/12.13
See application file for complete search history.

(56) References Cited

U.S. PATENT DOCUMENTS

| 1,000,304 A | * | 8/1911 | Sliger | F23L 13/00 |
| | | | | 126/285 R |
| 1,552,652 A | * | 9/1925 | Sauveur | G01N 3/52 |
| | | | | 73/79 |
| 2,579,503 A | | 12/1951 | Lubin et al. | |
| 2,755,658 A | | 7/1956 | Brown | |
| 2,778,406 A | | 1/1957 | Bramble et al. | |
| 3,038,330 A | * | 6/1962 | Criche | G01N 3/52 |
| | | | | 73/79 |
| 3,120,631 A | | 2/1964 | Morgan | |
| 3,426,578 A | | 2/1969 | Bergs et al. | |
| 3,787,022 A | * | 1/1974 | Wilcox | F16K 3/03 |
| | | | | 251/212 |
| 3,791,193 A | * | 2/1974 | Bole | G01N 3/303 |
| | | | | 73/12.13 |
| 3,896,657 A | | 7/1975 | Brandt et al. | |

(Continued)

FOREIGN PATENT DOCUMENTS

| DE | 432600 | 8/1926 |
| GB | 190811687 A | * 5/1909 |

(Continued)

OTHER PUBLICATIONS

Translation KR-20170074449-A (Year: 2017).*
International Search Report from International Patent Application No. PCT/US2018/014633, dated Mar. 23, 2018.

*Primary Examiner* — Natalie Huls
*Assistant Examiner* — Monica S Young
(74) *Attorney, Agent, or Firm* — Greer, Burns & Crain, Ltd.; Pradip Sahu; Philip T. Petti

(57) ABSTRACT

A ball drop iris is provided for use in a ball drop testing apparatus. Included on the iris is a lower housing having an upper mounting flange having a ball opening and a body depending from the flange, the body defining a passage through which a test ball passes. A control ring is disposed on the upper mounting surface for sliding, rotating action relative to the lower housing. A plurality of iris petals is provided, each operationally connected to the control ring and to the upper mounting flange to pivot between a closed position in which the ball opening is blocked, and an open position in which the petals are simultaneously retracted and the opening is clear for passage of a test ball.

9 Claims, 9 Drawing Sheets

(56) References Cited

U.S. PATENT DOCUMENTS

| | | | | |
|---|---|---|---|---|
| 4,202,527 A | * | 5/1980 | Price | B04B 11/02 |
| | | | | 251/212 |
| 4,336,710 A | * | 6/1982 | Miller | G01N 3/52 |
| | | | | 73/79 |
| 4,531,400 A | | 7/1985 | Nevel | |
| 5,033,519 A | * | 7/1991 | Puffer | B67D 7/365 |
| | | | | 137/421 |
| 8,074,489 B2 | | 12/2011 | Ishikawa et al. | |
| 9,206,911 B1 | * | 12/2015 | Daniels | F16K 27/045 |
| 2003/0128397 A1 | * | 7/2003 | Smith | G03B 17/08 |
| | | | | 358/296 |
| 2009/0087647 A1 | | 4/2009 | Nakagawa et al. | |
| 2012/0067426 A1 | * | 3/2012 | Soni | E21B 23/04 |
| | | | | 137/1 |

FOREIGN PATENT DOCUMENTS

| | | | |
|---|---|---|---|
| JP | 2001266759 | | 9/2001 |
| JP | 2008091044 | | 4/2008 |
| KR | 2011010030 | | 10/2011 |
| KR | 20160068185 A | | 6/2016 |
| KR | 20170074449 A | * | 6/2017 |
| WO | 2007048271 A1 | | 5/2007 |

\* cited by examiner

BALL DROP IRIS FOR VERTICAL IMPACT TESTING

BACKGROUND

The present device is generally related to materials testing equipment, more specifically to such equipment used for measuring the resistance of selected materials or structures to impact damage, and more particularly to the resistance of roofing structures and materials to environmental impact damage, for example from hail, falling branches or the like.

Underwriter's Laboratories (UL) has developed a test, known as UL 2218 for studying the resistance of various roofing materials to impact damage. A main objective of the test is to evaluate the resistance of target roofing structures to hail damage. A steel ball is dropped down a tube made of PVC plastic or the like, the pipe having a diameter large enough to accommodate the free fall of the steel ball. Ideally, the steel ball falls down the centerline of the pipe. The length of the pipe varies, depending on the diameter of the ball, with lengths of from 12-20 feet being customary. Impact damage by the ball falling on test roofing structure has been found to correlate with actual hail damage.

A steel fork having a pair of parallel tines spaced narrower than the diameter of the ball is transversely and slidably located near an upper end of the pipe, and is laterally retracted to initiate the ball drop. However, in practice, variations in the retraction of the fork, and the potential for the falling ball to contact the inner surface of the pipe create the possibility of inconsistent test results. Accordingly, there is a need for an improved ball drop test apparatus.

SUMMARY

The above-listed need is met or exceeded by the present ball drop iris, which is directed to a device used in impact testing of roofing materials, where a preferably 2-inch diameter steel ball is dropped from a prescribed height upon sample roof structures to test the ability to withstand impact. A feature of the present device is that the ball is uniformly held and released about the ball diameter for more consistent test results. The structure features a camera-lens type iris with petals preferably having recesses for retaining the ball in position prior to dropping. Each petal is preferably generally triangular in shape, with three corners, and a recessed ball seat for the test ball is located at one of the corners. Upon user activation of an external circular knob on the device, or remotely with the use of an electric solenoid, the iris petals are simultaneously retracted, so that the ball is released in a consistent manner.

More specifically, the present invention provides a ball drop iris for use in a ball drop testing apparatus. Included on the iris is a lower housing having an upper mounting flange having a ball opening and a body depending from the flange, the body defining a passage through which a test ball passes. A control ring is disposed on the upper mounting surface for sliding, rotating action relative to the lower housing. A plurality of iris petals is provided, each operationally connected to the control ring and to the upper mounting flange to pivot between a closed position in which the ball opening is blocked, and an open position in which the petals are simultaneously retracted and the opening is clear for passage of a test ball.

In another embodiment, a ball drop test apparatus is provided, including a ball drop tube having an upper end and a lower end. A ball drop iris is mounted at the upper end and is constructed and arranged for dropping a test ball down the ball drop tube under operator control. The ball drop iris is provided with a lower housing having an upper mounting flange having a ball opening and a body depending from the flange, the body defining a passage through which a test ball passes. A control ring is disposed on the upper mounting surface for sliding, rotating action relative to the lower housing. A plurality of iris petals is provided, each connected to the control ring and to the upper mounting flange to pivot between a closed position in which the ball opening is blocked, and an open position in which the opening is clear for passage of a test ball.

DETAILED DESCRIPTION

Figure 1:
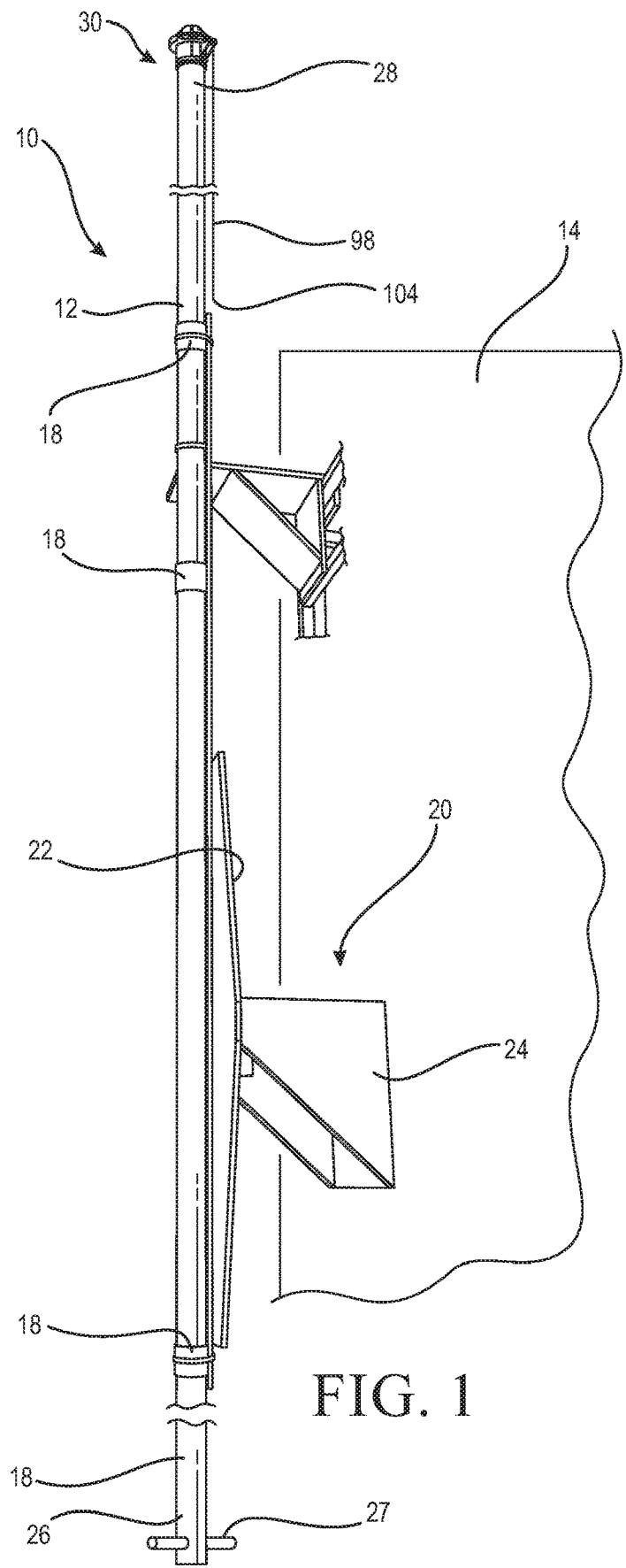
FIG. 1 is a fragmentary front view of a ball drop testing apparatus equipped with the present ball drop iris.
Figure 4:
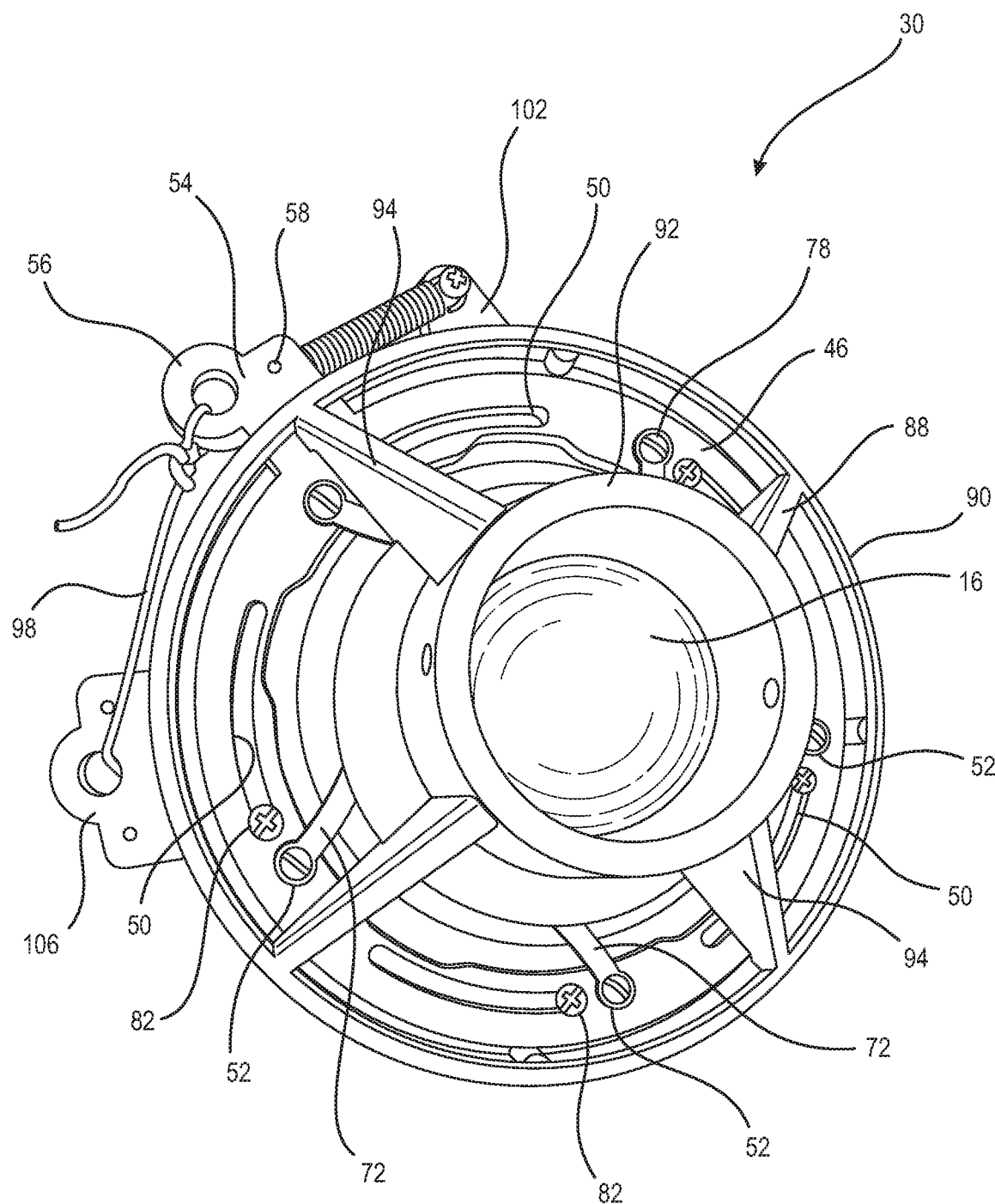
FIG. 4 is a top perspective view of the present ball drop iris with a test ball in position.

Referring now to FIG. 1, a ball drop test apparatus is generally designated 10, and includes an elongate tube 12 which is at least temporarily fixed to a substrate 14 such as a wall. The tube 12 is preferably made of plastic, such as PVC, however other self-supporting materials are contemplated. A diameter of the tube 12 is selected to accommodate the free fall of a steel test ball 16 (FIG. 4). In the preferred embodiment, the test ball 16 has a 2-inch (50.8 mm) diameter, the tube 12 has a diameter of 3-inches (76.2 mm) and a length of 20 feet (6.1 meters). As seen in FIG. 1, the tube 12 is optionally assembled from several sections held together end-to-end by conventional PVC plumbing couplers 18. Also, a pivot bracket 20 is used to secure the tube 12 to the substrate 14. A support panel 22 is pivotally mounted to a base 24 about a pivot point (not shown) so that the tube can be rotated to a generally horizontal position to facilitate maintenance by an operator as needed. A lower end 26 of the tube is optionally provided with a removable locking pin 27.

Opposite the lower end 26, an upper end 28 of the tube 12 is provided with the present ball drop iris, generally designated 30. To address the above-listed drawback of the prior art test devices, the present ball drop iris 30 features a mechanism whereby the test ball 16 is released uniformly so that the descent of the ball is down the center of the tube 12. The operation of the present ball drop iris 30 will be disclosed in greater detail below.

Figure 2:
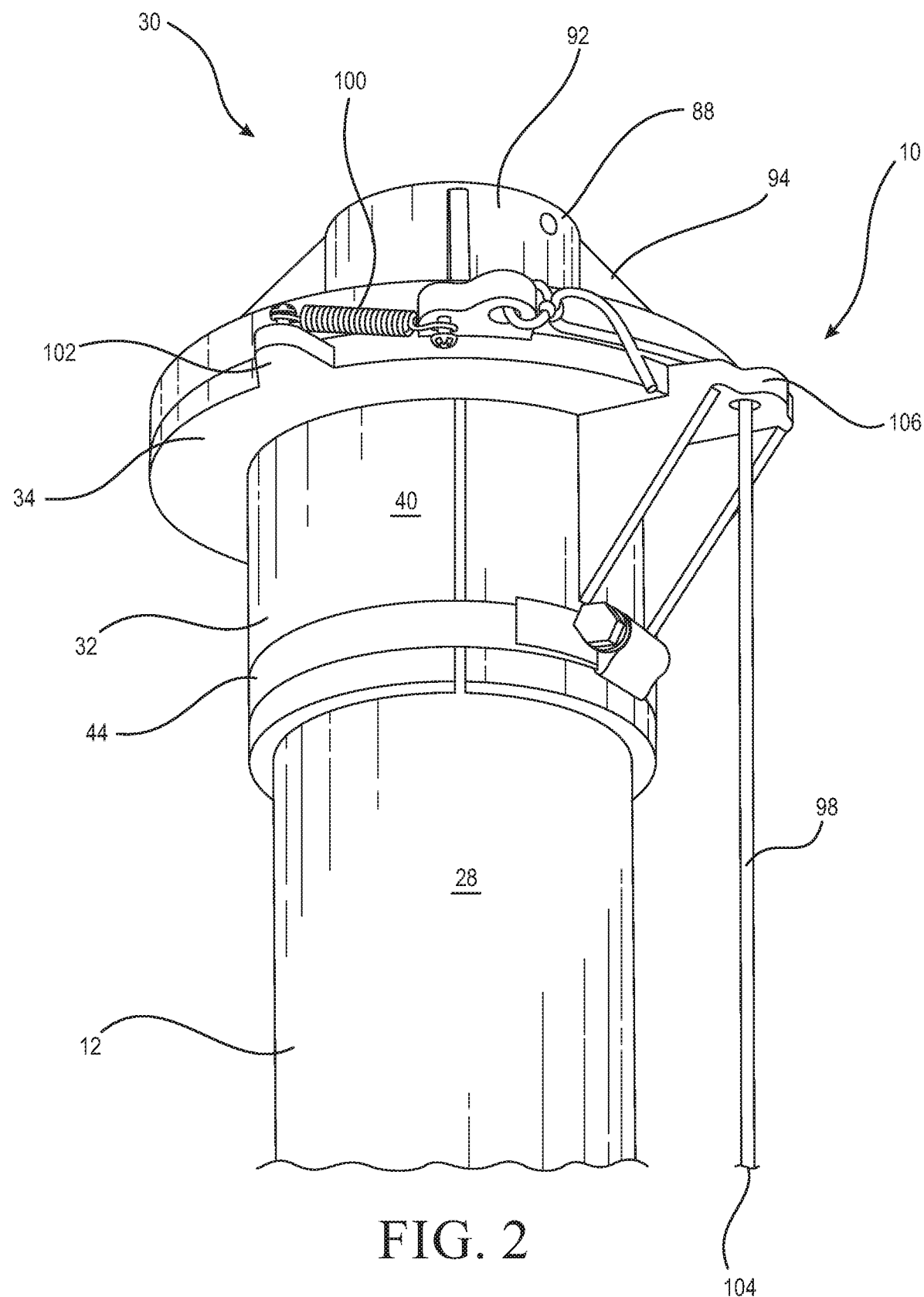
FIG. 2 is an enlarged fragmentary perspective view of the top of the ball drop apparatus of FIG. 1 including the present ball drop iris.
Figure 3:
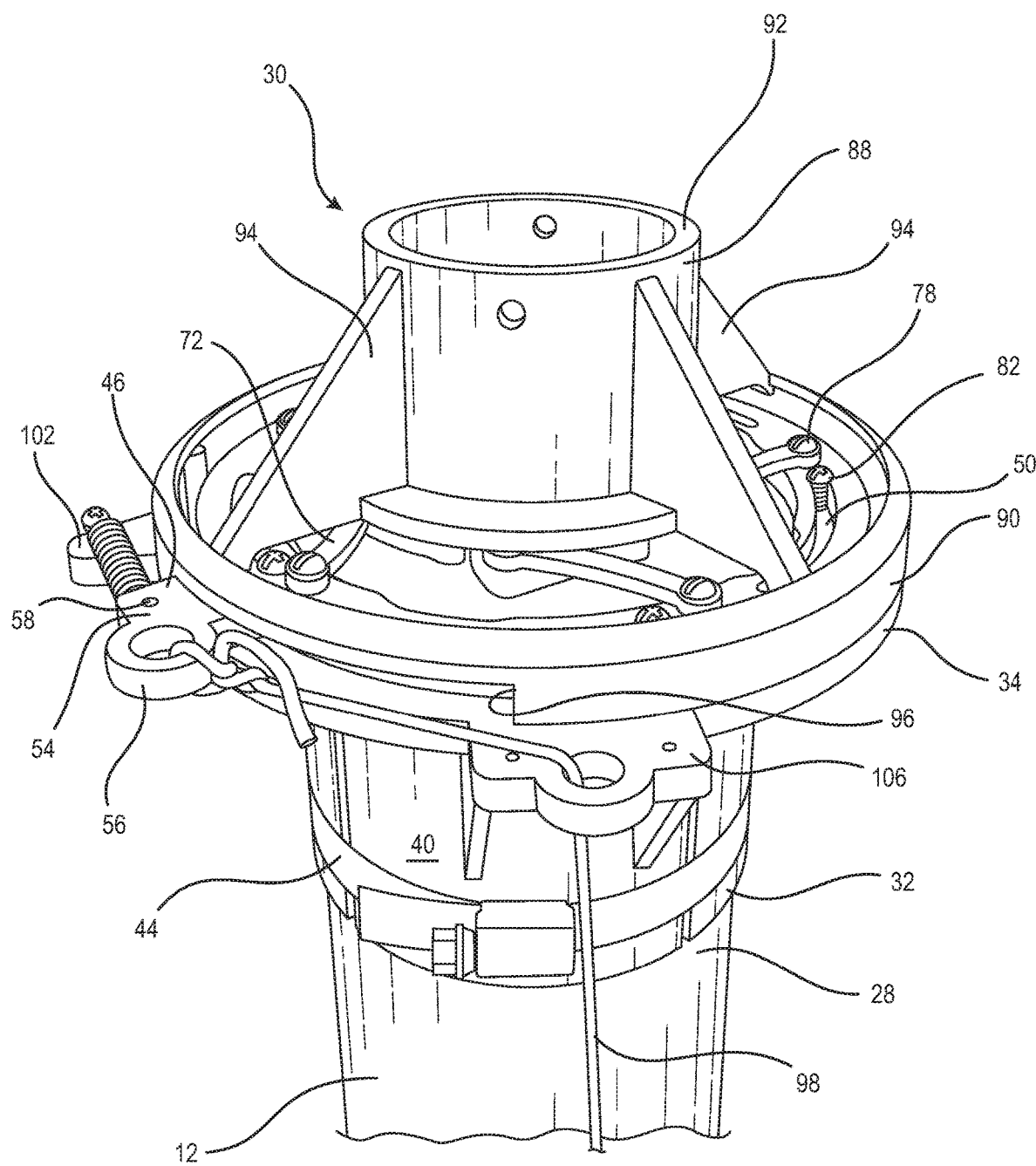
FIG. 3 is a top perspective view of the present ball drop iris mounted on the present testing apparatus.

Referring now to FIGS. 2, 3, 8 and 9, included on the ball drop iris 30 is a lower housing 32 having an upper mounting flange 34 with an upper surface 36 having a ball opening 38 (FIG. 8) and a body 40 depending from the flange. In the preferred embodiment, the body 40 is generally cylindrical in shape and is dimensioned to matingly accommodate the tube upper end 28, however other shapes are contemplated. Also, the body defines a passage 42 (shown hidden) through which the test ball 16 passes. The ball opening 38 is in communication with the passage 42. In addition, the body 40 is formed in at least two segments 40a, 40b (FIGS. 8 and 9) and as such is secured atop the upper end 28 of the tube 12, such as by being clamped by a hose clamp 44 or the like (FIGS. 2 and 3).

Figure 8:
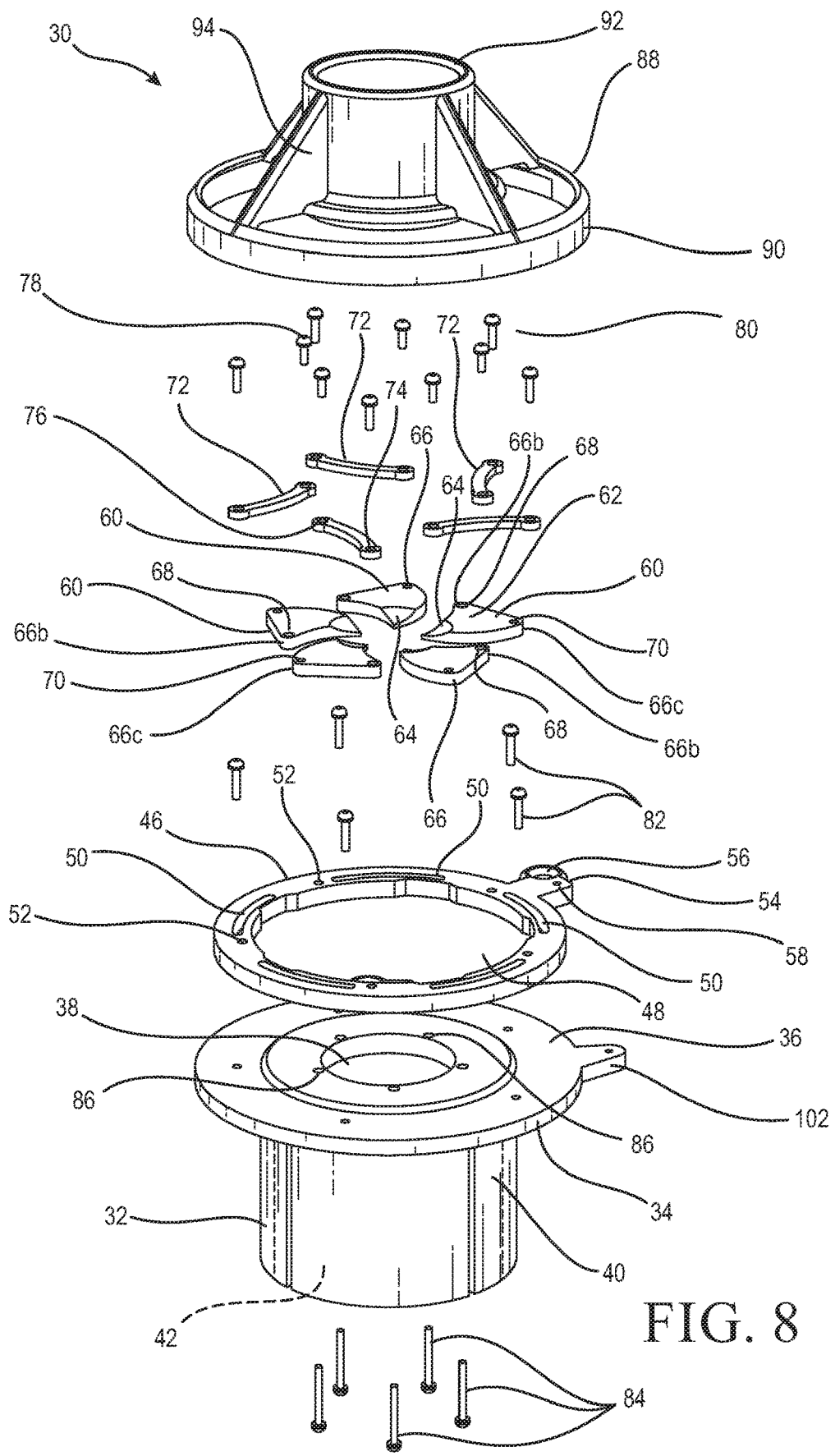
FIG. 8 is an exploded perspective view of the present ball drop iris.
Figure 9:
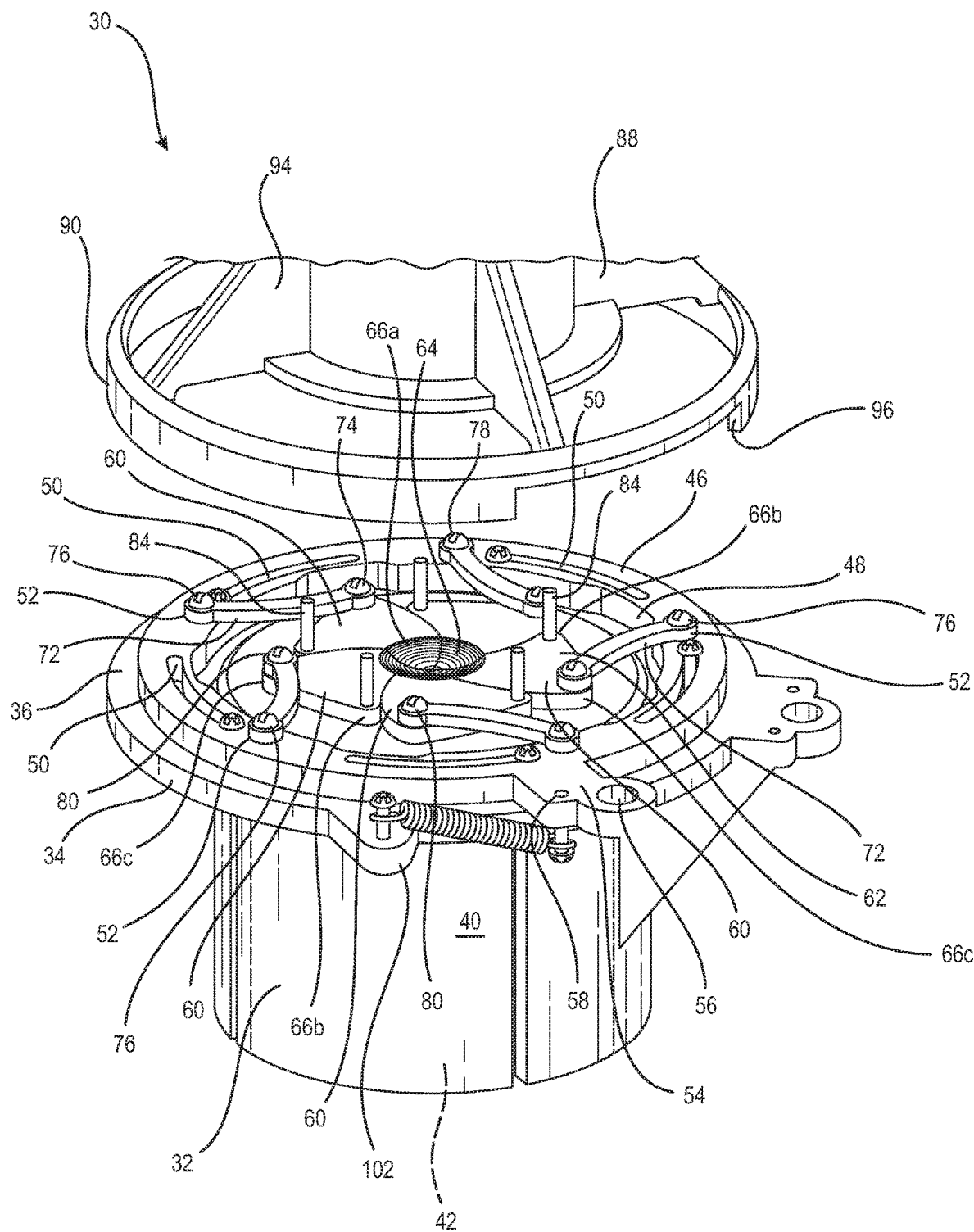
FIG. 9 is a fragmentary perspective partially exploded view of the present ball drop iris.

Referring now to FIGS. 4, 8 and 9, a control ring 46 is disposed on the upper surface 36 of the flange 34 for sliding, rotating action relative to the lower housing 32. While other dimensions are contemplated, the control ring 46 is preferably of a diameter that is slightly less than that of the flange 34; and defines a central open space 48 which surrounds the ball opening 38. At least one and preferably a plurality of arcuate locating slots 50 are cut into the ring, as well as at least one and preferably a plurality of link mounts 52. In addition, an actuator lug or tab 54 projects radially from a periphery of the control ring 46 and has an operator line mount eyelet 56, and a spring mount 58 (FIG. 8). In the preferred embodiment, the eyelet 56 and the spring mount 58 are located on opposite sides of the lug 54, however other arrangements are contemplated.

Also located within the open space 48 defined by the control ring 46 is a plurality of iris petals 60, each operationally connected to the control ring 46 and to the mounting flange 34 to pivot between a closed position (FIG. 5) in which the ball opening 38 is blocked, and an open position (FIG. 6) in which the petals are simultaneously retracted and the opening is clear for passage of the test ball 16 down the tube 12.

Referring now to FIGS. 8 and 9, in the preferred embodiment, each of the petals 60 has an upper surface 62 contacting the test ball 16, and featuring a recessed ball seat 64. Further, it is preferred that each petal 60 is generally triangular in shape when viewed from above as the iris is oriented in FIGS. 5 and 6 and has three corners 66, with the recessed ball seat 64 located at one corner 66a, a pivot aperture 68 located at a second corner 66b, and a link aperture 70 located at a third corner 66c.

As seen in FIGS. 8 and 9, the present ball drop iris 30 also includes a plurality of link arms 72, being somewhat arcuate in shape, and each having a first end opening 74 for connection to the link aperture 70 of an associated petal 60, and an opposite second end opening 76 for connection to a corresponding one of the link mounts 52 on the control ring 46. The exact shape of the link arms 72 is variable depending on the application.

Fasteners 78, typically screws or the like, secure the second end openings 76 to the link mounts. As such, rotation of the control ring 46 causes simultaneous movement of the link arms 72. In addition, fasteners 80, also screws or the like, connect the first end openings 74 of the link arms 72 to the link apertures 70 on the petals 60. Further, fasteners 82, preferably screws or the like pass through the locating slots 50 in the control ring 46 and engage the upper surface 36 of the flange 34. As such, the fasteners 82 define and guide the rotational movement of the control ring 46 relative to the lower housing 32. Lastly, another group of fasteners 84 (FIG. 8), also referred to as pivot pins, and preferably being screws with threads concentrated at the tips, are positioned within the passage and pass through guide apertures 86 in the flange 34 disposed about the ball opening 38, pass through the pivot apertures 68 in the petals 60, and threadably engage suitable threaded closed end bores (not shown) in an upper housing 88, thus securing the upper housing to the lower housing 32 with the control ring 46 and the petals sandwiched between. Unthreaded portions of the fasteners 84 serve as pivot points for rotation by the petals 60.

Figure 5:
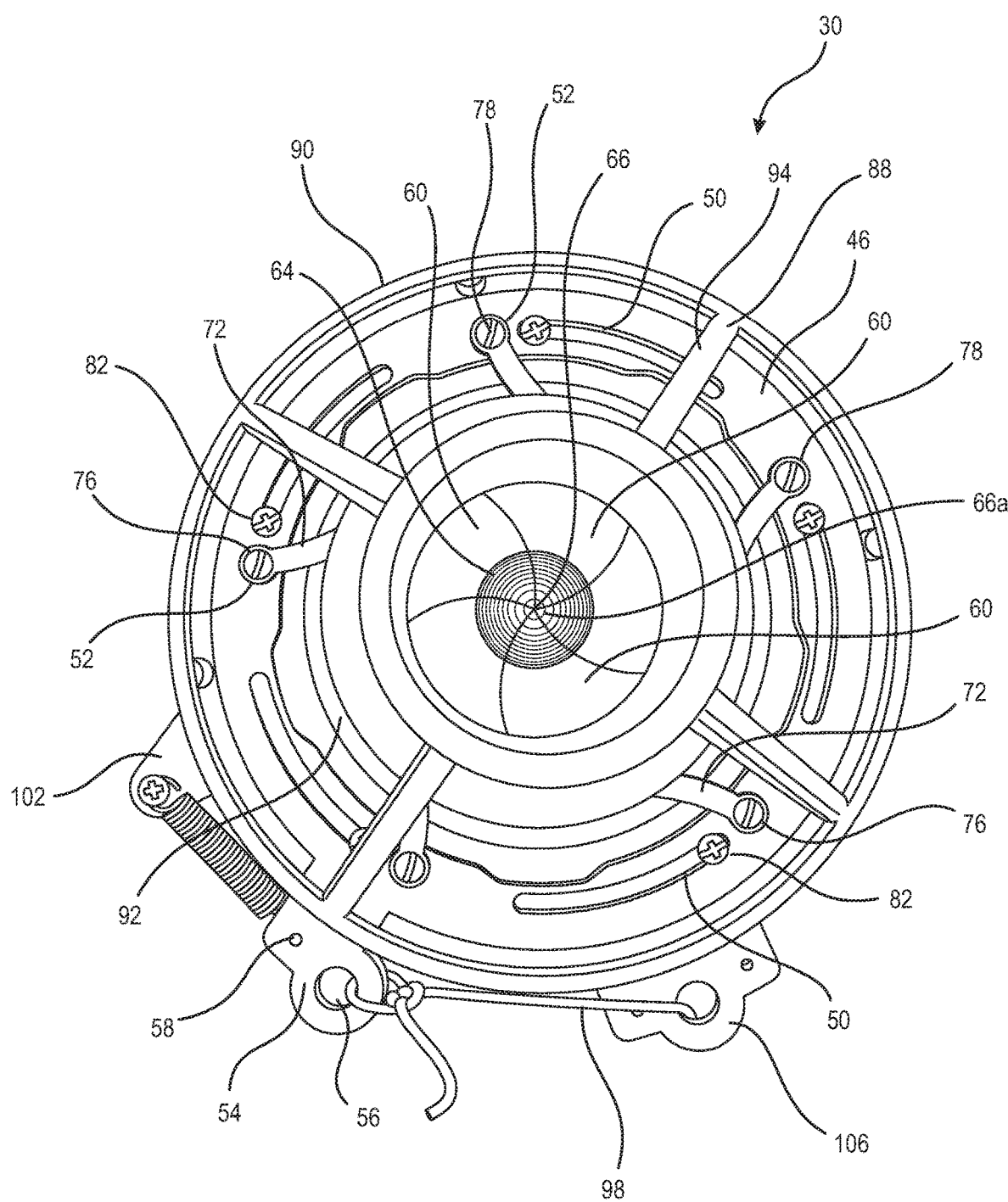
FIG. 5 is a top plan view of the present ball drop iris in a closed position.

Included on the upper housing 88 is a depending skirt 90 that circumscribes the control ring 46, and a ball inlet tube 92 in registry with the ball opening 38 and the petals 60. Support trusses 94 preferably connect the skirt 90 to the ball inlet tube 92. Also, notches 96 (FIG. 9) in the depending skirt 90 accommodate the movement of the actuator lug 54 as it moves between the open and closed positions of the iris. An operator line 98 such as a cord, string, wire or the like, is secured at one end to the operator line mount eyelet 56, and a biasing element 100, preferably a coiled spring, is connected at one end to the spring mount 58 and at the opposite end to a spring tab 102 extending radially from the flange 34. The biasing element 100 urges the control ring 46 to a rest or closed position (FIG. 5), in which the petals 60 are closed. A free end 104 of the operator line extends approximately to the lower end 26 of the tube 12, and in any event is long enough to reach the operator. An optional line guide 106 is also provided to the flange 34, extending radially therefrom (FIGS. 4 and 5).

Figure 6:
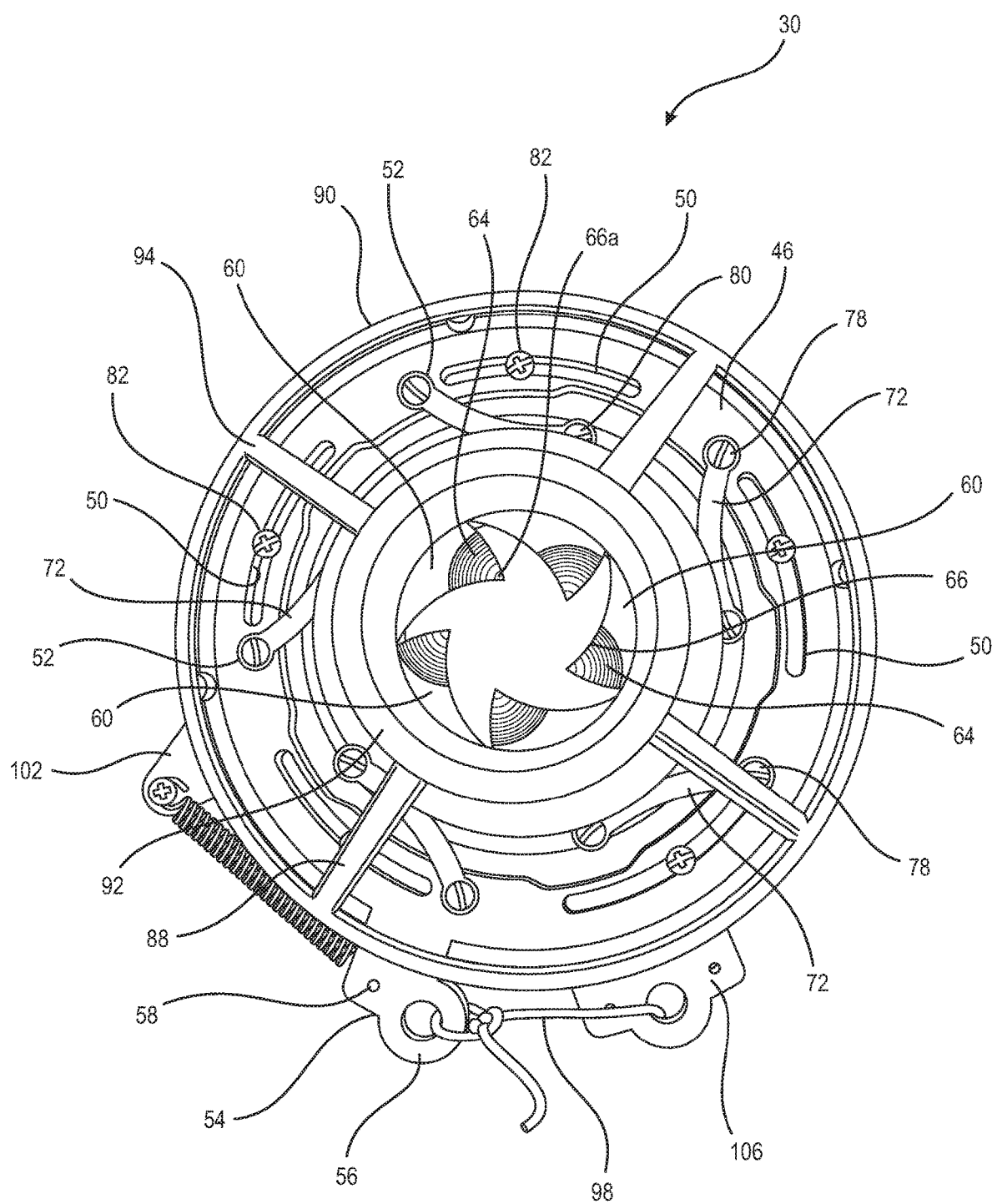
FIG. 6 is a top plan view of the present ball drop iris in an open position.
Figure 7:
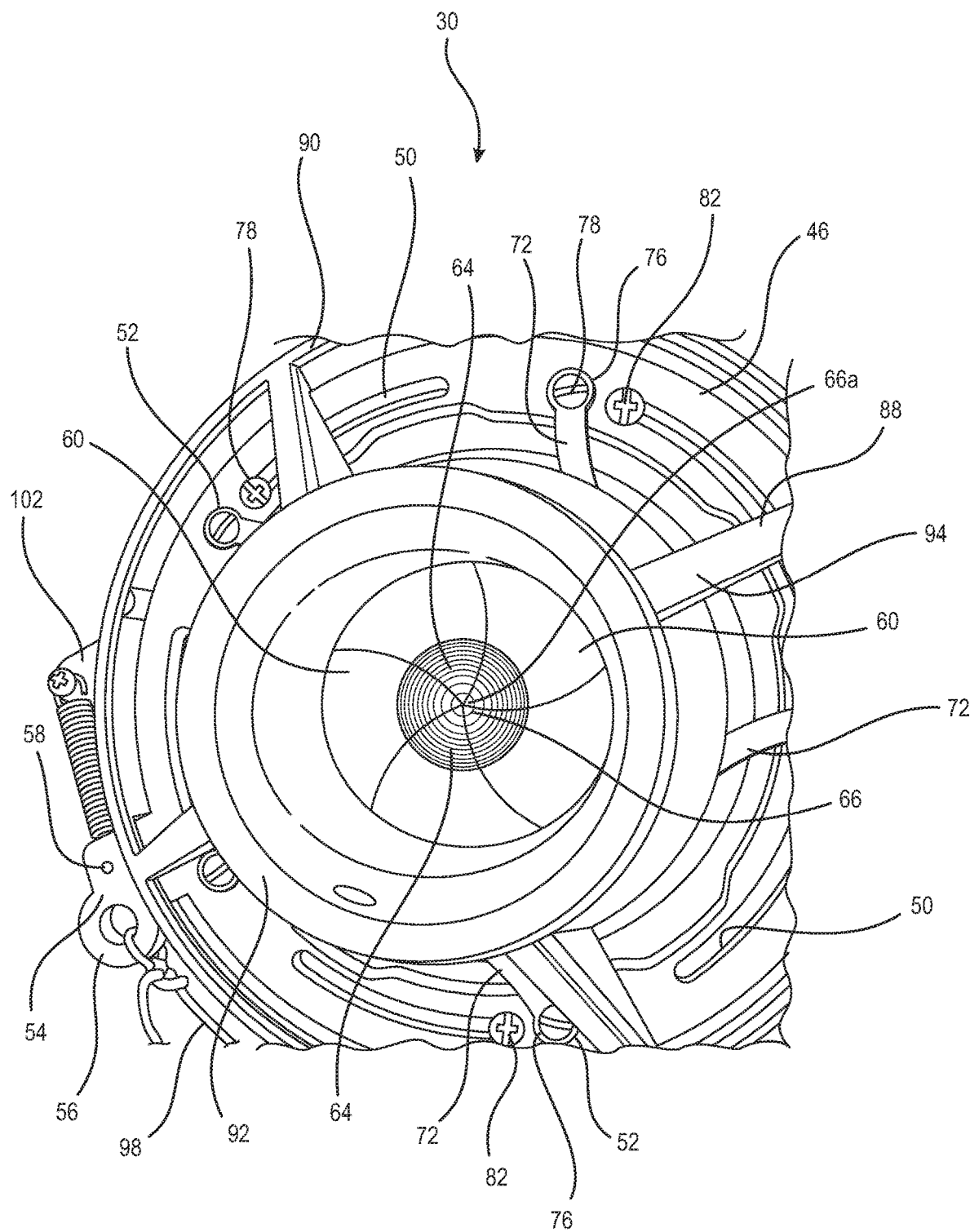
FIG. 7 is an enlarged top perspective view of the present ball drop iris in the closed position.

Referring now to FIG. 4, upon assembly, the test ball 16 is placed in the ball inlet tube 92 and rests upon the recessed ball seat 64. Once the structure to be tested is placed below the lower end 26 of the tube 12, the operator pulls on the operator line 98, which rotationally draws the control ring 46 against the force of the biasing element 100 and along the track formed by the locating slots 50. During this process, the link arms 72 pull all of the petals 60 simultaneously from the closed position (FIG. 5) to the open position (FIG. 6). As the petals 60 retract, the test ball 16 is dropped down the center of the tube 12 to impact the structure to be tested. In this manner, the test ball 16 is dropped more consistently than in conventional vertical impact test devices.

While a particular embodiment of the present ball drop iris has been described herein, it will be appreciated by those skilled in the art that changes and modifications may be made thereto without departing from the invention in its broader aspects and as set forth in the following claims.

The invention claimed is:

1. A ball drop iris for use in a ball drop testing apparatus, comprising: a lower housing having an upper mounting flange having a ball opening and a body depending from said flange, said body defining a passage through which a test ball passes; a control ring disposed on said upper mounting flange for sliding, rotating action relative to said lower housing and relative to said upper mounting flange; a plurality of iris petals each operationally connected to said control ring and to said upper mounting flange to pivot between a closed position in which said ball opening is blocked, and an open position in which said petals are simultaneously retracted and said opening is clear for passage of a test ball; said control ring includes an actuator lug having a radially projecting eyelet configured for connection to a control line; and a biasing element is connected at one end to said actuator lug, and at an opposite end to said mounting flange, wherein each said petal pivots in a direction transverse to a direction of travel of the test ball and has an upper surface contacting said ball, said upper surface provided with a recessed ball seat.

2. The ball drop iris of claim 1 wherein when said iris is in said closed position, the test ball is located upon said ball seats of said iris petals.

3. The ball drop iris of claim 1, wherein said control ring is connected to said biasing element that is connected to said upper mounting flange, said biasing element generating a rotational biasing force urging said petals to the closed position.

4. The ball drop iris of claim 1 further including a plurality of link arms, each said arm connected at a first end to an associated one of said petals at a link aperture, and at an opposite end to said control ring.

5. The ball drop iris of claim 4, wherein each said petal also has a pivot aperture configured for accommodating a pivot pin secured to said flange.

6. The ball drop iris of claim 5, wherein each said petal is generally triangular in shape, with three corners, and said pivot aperture, said link aperture and a recessed ball seat are located at distinct corners.

7. The ball drop iris of claim 5, wherein each said petal is generally triangular in shape, with three corners, and a recessed ball seat for the test ball is located at one of said corners.

8. The ball drop iris of claim 1, further including an upper housing attachable to said lower housing with said control ring and said petals sandwiched between, and including a ball entry tube dimensioned to slidably accommodate the test ball and being in registry with said passage.

9. A ball drop iris for use in a ball drop testing apparatus, comprising:

a lower housing having an upper mounting flange having a ball opening and a body depending from said flange, said body defining a passage through which a test ball passes;

a control ring disposed on said upper mounting flange for sliding, rotating action relative to said lower housing and relative to said upper mounting flange;

at least three iris petals, each operationally connected to said control ring and to said upper mounting flange to pivot between a closed position in which said ball opening is blocked, and an open position in which said petals are simultaneously retracted and said opening is clear for passage of a test ball;

a plurality of link arms, each said arm associated with one said iris petal, connected at a first end to an associated one of said petals at a link aperture, and at an opposite end to said control ring;

each said petal also has a pivot aperture configured for accommodating a pivot pin secured to said flange; and each said petal is generally triangular in shape, with three corners, and said pivot aperture, said link aperture and a recessed ball seat are located at distinct corners on each said petal.

* * * * *